United States Patent [19]

Pensak et al.

[11] 3,947,570

[45] Mar. 30, 1976

[54] ORAL PRODUCT

[75] Inventors: Philip Pensak, New Brunswick;
Joseph P. Januszewski, Somerville, both of N.J.

[73] Assignee: Colgate-Palmolive Company, New York, N.Y.

[22] Filed: Nov. 22, 1974

[21] Appl. No.: 526,446

Related U.S. Application Data

[62] Division of Ser. No. 304,040, Nov. 6, 1972, Pat. No. 3,864,472.

[52] U.S. Cl. .................. 424/54; 424/49; 424/58
[51] Int. Cl.² .................. A61K 7/22; A61K 7/26
[58] Field of Search .................. 424/49–58; 426/221–223

[56] References Cited
UNITED STATES PATENTS

| | | | |
|---|---|---|---|
| 1,275,275 | 8/1918 | Levinson | 424/55 |
| 3,462,525 | 8/1969 | Levinsky et al. | 424/57 |
| 3,514,513 | 5/1970 | Bechtold | 424/54 |
| 3,639,569 | 2/1972 | Medcalf | 424/54 |
| 3,666,855 | 5/1972 | Muhler | 424/54 |
| 3,703,583 | 11/1972 | Martin | 424/54 |
| 3,864,472 | 2/1975 | Pensak et al. | 424/54 |

*Primary Examiner*—Shep K. Rose
*Attorney, Agent, or Firm*—Steven J. Baron; Murray M. Grill; Herbert Sylvester

[57] ABSTRACT

A stable, visually clear, haze free, lemon oil containing flavored mouthwash free from unpleasant tasting lemon oil degradation components comprising water, lemon oil, nonionic surfactant, humectant and buffering agent.

18 Claims, No Drawings

ORAL PRODUCT

This is a divisional of application Ser. No. 304,040 filed Nov. 6, 1972, now U.S. Pat. No. 3,864,472; issued on Feb. 4, 1975, the benefit of which filing date is claimed.

The invention pertains to a liquid mouthwash formulation. Specifically, the invention relates to a visually clear, stable mouthwash having the stimulating and refreshing taste of lemon. More specifically, the invention provides a stable aqueous mouthwash containing a suitable lemon flavoring ingredient, typically lemon oil, lemon juice or a combination thereof.

Liquid mouthwashes are specifically formulated to provide a comfortable feeling in the mouth during use. Advantageously, a suitable mouthwash product should have a low enough viscosity to permit the user to readily manipulate and swish it around in his mouth to effectively gargle. Accordingly, the viscosity of a suitable product in accordance with the invention should be well below 1000 cps preferably less than about 100 cps at room temperature, e.g., from about 1.0 to about 10.0 cps.

To obtain consumer acceptance, a mouthwash formulation must have a pleasant flavor. The use of certain specific flavoring ingredients, such as lemon oil for example, may introduce stability and/or compatibility problems in an aqueous mouthwash composition.

The use of lemon oil flavoring in such compositions may result in a hazy product or in the settling out of certain components during storage. These undesirable characteristics of a lemon oil flavored aqueous mouthwash may be due to the presence of a high percentage of non-polar terpene components in lemon oil. An additional problem that may arise in an aqueous lemon oil flavored mouthwash is the natural degradation of the lemon oil component which can result in an unpleasant tasting product.

It is a primary advantage of the present invention to provide an emulsifying ingredient for lemon oil flavored mouthwash formulations that results in a clear, stable product. A further advantage of the invention is to provide a pH range for aqueous lemon oil containing mouthwash compositions wherein the unpleasant tasting products of the material degradation of lemon oil are minimized.

The mouthwash composition according to the invention typically contains from about 60 to about 95 percent, preferably 70 to 80, e.g., about 75 percent by weight water and from about 0 to about 25, preferably 5 to 24, e.g., about 15 percent by weight of non-toxic alcohol such as isopropanol and ethanol. The alcohol component of the mouthwash preferably utilizes denaturing components which also function as flavoring agents. These materials are exemplified by the following materials: anethol, anise oil, bay oil (cyrcia oil), benzaldehyde, bergamot oil, bitter almond oil, camphor, cedar leaf oil, chlorothymol, cinnamic aldehyde, cinnamon oil, citronella oil, clove oil, coal tar, eucalyptol, eucalyptus oil, eugenol, guaiacol, lavender oil, menthol, mustard oil, peppermint oil, phenol, phenyl salicylate, pine oil, pine needle oil, rosemary oil, sassafras oil, spearmint oil, spike lavender oil, storax, thyme oil, thymol, tolu balsam, turpentine oil, wintergreen oil and boric acid. The denaturing agents are typically present in an amount between about 1 and 2 percent of the total alcohol content of the mouthwash.

In one specific aspect, the invention provides a nonionic surfactant ingredient that effectively emulsifies the lemon oil component in an aqueous mouthwash resulting in a clear, stable formulation. According to this aspect of the invention, the surfactant ingredient is chosen from the group of nonionic surface active agents consisting of polyoxyethylene derivatives of sorbitan mono- di- and tri-fatty acid esters wherein the fatty acid component has between 12 and 24 carbon atoms and the polyoxyethylene chains contain from about 4 to about 30 ethylene oxide units and at least 40 percent of the molecular weight of the molecule is ethylene oxide. Representative derivatives include polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate. Particularly preferred is polyoxyethylene sorbitan monoisostearate containing 20 oxyethylene units per molecule. The preferred polyoxyethylene (20) sorbitan monoisostearate emulsifier is a liquid material at room temperature and does not adversely affect the flavoring characteristics to the formulation when used in accordance with the invention.

The surfactant component of the new formulation should be present in an adequate amount to completely emulsify the lemon oil flavoring component to produce a clear, stable product. The concentration of emulsifier is typically from about 0.1 to 5 percent of the formulation depending on the alcohol content and lemon oil concentration. The amount of surfactant should be greater for higher amounts of the lemon oil flavoring component and less for smaller amounts of lemon oil. Pursuant to the invention, to obtain a clear, stable lemon oil containing aqueous mouthwash the weight ratio of surfactant to lemon oil in the new formulation should be at least 1.5 to 1, preferably about 10 to 1, for a formulation containing about 15 percent alcohol; less for higher alcohol formulations. For non-alcohol containing formulations the weight ratio of emulsifier to lemon oil flavoring should be at least 5 to 1 to obtain a clear, stable product.

The lemon oil flavoring component is preferably derived from the rind of lemons by methods well known in the art. The lemon oil component of the formulation is present in an amount from about 0.01 to about 1%, typically from 0.05 to 1.0%, most preferably about 0.1 to 0.5%, e.g., 0.2% by weight depending on the flavoring effect desired. Of course, an equivalent synthetic lemon oil component may be used if desired.

In addition to, or instead of, the lemon oil component, lemon juice which is derived from the pulp of lemons, can be included in the mouthwash formulation to further accent the flavor of the product. In its natural state, lemon juice can also include lemon oil in amounts ranging from 0.25 percent to about 1 percent, typically about 0.5 percent. When included in combination with lemon oil, lemon juice can be present in any suitable amount, typically from about 5 to 15 percent of the formulation. When used instead of lemon oil to flavor an aqueous mouthwash, lemon juice should be present in an amount resulting in an equivalent lemon oil concentration, as previously defined.

The mouthwash composition preferably contains glycerine in amounts up to about 15 percent, with compositions containing between about 8 and 12 percent having particularly desirable characteristics. The glycerine functions as a sweetener, supplies "body" to the compositions and a "velvety" feel in the mouth. It may be replaced in whole or in part by such equivalent materials as sorbitol or propylene glycol.

The mouthwash composition may also optionally contain small effective amounts of antibacterial agents such as the quaternary ammonium compounds and the substantially saturated aliphatic acyl amides. Preferred additions of these agents are in amounts between about 0.01 and 0.1 percent. The following are illustrative of useful antibacterial agents: benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmitoyl sarcosine, lauroyl sarcosine, N-hyristoyl glycine, and potassium N-lauroyl sarcosine.

The mouthwash composition will usually also contain adjuvant materials to provide color, additional flavoring if desired, and sweetening effects. Color is typically added in an amount up to about 0.01 percent. Additional flavorant, such as citric acid, or sweetener, such as saccharin, is preferably added in small amounts from about 0.01 to about 0.1 percent, typically about 0.05 percent.

Pursuant to a further specific aspect of the invention, the pH of the mouthwash formulation is adjusted to from about 3.5 to about 7.0, preferably from about 5 to 6, by the inclusion of a buffering material. By providing the mouthwash with a pH from about 3.5 to about 7.0, preferably from about 5 to about 6, it has been found that the products formed by natural degradation of the lemon oil component due to oxidation catalyzed by sunlight are surprisingly not as unpleasant tasting as those found in an equivalent formulation having a pH below about 3.5. The buffering ingredient can be any suitable alkaline material that does not adversely affect the flavor of the formulation.

According to this aspect of the invention, a sufficient amount of the buffering ingredient to raise the pH of the formulation to the desired level, preferably between about 5 and 6, is included in the lemon oil containing mouthwash. Typically, the buffering ingredient is present in an amount from about 0.1 to about 1.0 percent by weight, preferably about 0.5 percent. Suitable buffering materials are alkali metal salts of weak organic acids such as sodium benzoate, sodium citrate, potassium tartrate and sodium phosphate.

The mouthwash composition can be prepared by methods well known in the art, typically by combining the specified components in an amount of water sufficient to bring the total of the components to 100 percent. It is preferable to admix the alcohol-soluble components in the alcohol in a suitable mixing vessel and then add water to the vessel. Components of the mouthwash composition which have greater solubility in water than alcohol are preferably added to the water before it is admixed with the alcohol mixture or added to the composition after the water addition.

The following specific examples are further illustrative of the nature of the present invention, but the invention is not limited thereto. All amounts and percentages through the specification and in the claims are by weight unless otherwise indicated.

EXAMPLE 1

The following mouthwash is formulated:

|  | Percent by Weight |
|---|---|
| Denatured ethanol (95%) | 15.00 |
| Polyoxyethylene (20) sorbitan monoisostearate | 1.00 |
| Benzethonium chloride | 0.03 |
| Lemon oil | 0.20 |
| Glycerine | 10.00 |
| Sodium saccharin | 0.04 |
| Color (FD&C yellow No. 5; 0.01% solution) | 0.60 |
| Deionized water | 73.13 |
|  | 100.00 |

The denaturing components of the ethanol contain flavoring materials. This formulation is visually clear with a yellow tint, does not separate during prolonged storage and has a refreshing lemon taste.

EXAMPLE 2

The formulation of Example 1 is reformulated to include 25 percent by weight of 95 percent ethanol with a corresponding decrease in the amount of water present.

EXAMPLE 3

The following mouthwash is formulated:

|  | Percent by Weight |
|---|---|
| Denatured alcohol (95%) | 15.00 |
| Polyoxyethylene (20) sorbitan monoisostearate | 1.00 |
| Lemon oil | 0.20 |
| Sodium benzoate | 0.50 |
| Benzethonium chloride | 0.03 |
| Glycerine | 10.00 |
| Sodium saccharin | 0.04 |
| Color (FD&C yellow No. 5; 0.01% solution) | 0.60 |
| Deionized water | 72.63 |
|  | 100.00 |

The denaturing components of the ethanol contain flavoring materials. This formulation is visually clear with a yellow tint, does not separate during prolonged storage and has a refreshing lemon taste and a pH of about 5.5.

EXAMPLE 4

The formulation of Example 3 is reformulated to include 25 percent of 95 percent ethanol with a corresponding decrease in the amount of water present.

EXAMPLES 5–10

The following mouthwashes having lemon flavors of varying intensities are formulated:

| Ingredient | Example Number; Percent by Weight | | | | | |
|---|---|---|---|---|---|---|
|  | 5 | 6 | 7 | 8 | 9 | 10 |
| Denatured alcohol (95%)[1] | — | — | 10.0 | 20.0 | 25.00 | 18.00 |
| Emulsifier[2] | 0.5 | 2.00 | 0.5 | 5.0 | 2.00 | 1.00 |
| Lemon oil | 0.1 | 0.20 | 0.2 | 1.0 | 0.10 | 0.20 |
| Antimicrobial agent[3] | 5.0 | — | 0.5 | 0.8 | 0.50 | 0.05 |
| Glycerine[4] | — | — | 10.0 | 15.0 | — | 15.00 |
| Buffering agent[5] | — | 0.50 | — | 1.0 | — | 0.50 |
| Lemon juice | — | 10.00 | — | — | 10.00 | 5.00 |

-continued

| Ingredient | Example Number; Percent by Weight | | | | | |
|---|---|---|---|---|---|---|
| | 5 | 6 | 7 | 8 | 9 | 10 |
| Sweetener[6] | — | — | — | 0.1 | 0.06 | 0.10 |
| Additional flavorant[7] | — | 0.05 | — | 0.1 | — | 0.05 |
| Deionized water | 94.3 | 87.85 | 78.3 | 62.0 | 62.34 | 60.10 |

[1]Ethanol or isopropanol
[2]Preferably polyoxyethylene (20) sorbitan monoisostearate; polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate and polyoxyethylene sorbitan trioleate can also be used
[3]Preferably benzethonium chloride; diisobutyl phenoxyethoxy ethyl dimethyl benzyl ammonium chloride, N-alkylpyridinium chloride, N-cetyl pyridinium bromide, sodium N-lauroyl sarcosine, sodium N-palmitoyl sarcosine, lauroyl sarcosine, N-myristoyl glycine and potassium N-lauroyl sarcosine can also be used
[4]Sorbitol or propylene glycol can be substituted for glycerine
[5]Sodium benzoate, sodium citrate, potassium tartrate or sodium phosphate
[6]Sodium saccharin
[7]Citric acid The formulations of Examples, 5, 7, and 8 are visually clear and stable. Due to the presence of lemon juice, the formulations of Examples 6, 9 and 10 are hazy and contain settleable solids. They can be filtered to obtain a clear stable product.

Although the present invention has been described with reference to particular embodiments and examples, it will be apparent to those skilled in the art that variations and modifications of this invention can be made and that equivalents can be substituted therefor without departing from the principles and true spirit of the invention.

What is claimed is:

1. A stable, visually clear, haze free, lemon oil-containing flavored mouthwash free from unpleasant tasting lemon oil natural degradation components comprising from about 60 to about 95 percent by weight of water, about 0.01 to about 1.0 percent by weight of lemon oil, about 0.1 to about 5.0 percent by weight of a nonionic surfactant chosen from the group consisting of polyoxyethylene derivatives of sorbitan mono-, di- and tri-fatty acid esters wherein the fatty acid component has between 12 and 24 carbon atoms and the polyoxyethylene chains contain about 4 to about 30 ethylene oxide units and at least 40 percent by the molecular weight of the molecule is ethylene oxide, from 0 to about 25 percent by weight of a non-toxic alcohol, about 8 to 15 percent by weight humectant and a sufficient amount of a buffering agent to maintain a pH for said mouthwash of about 3.5 to about 7.0.

2. A mouthwash according to claim 1, wherein the weight ratio of said surfactant to said lemon oil is greater than 1.5 to 1.

3. A mouthwash according to claim 1, wherein said alcohol is ethanol or isopropanol and is present in an amount of about 5 to about 25 percent by weight.

4. A mouthwash according to claim 1, further including an effective amount of an anti-bacterial agent chosen from the group consisting of a quaternary ammonium and aliphatic acyl amide germicides having an anti-bacterial activity.

5. A mouthwash according to claim 2, wherein said lemon oil is present in an amount from about 0.1 to about 0.5 percent by weight and said weight ratio is at least 5 to 1.

6. A mouthwash according to claim 1, wherein the weight ratio of said surfactant to said lemon oil is about 10 to 1.

7. A mouthwash according to claim 1, further including from about 5 to about 15 percent by weight of lemon juice.

8. A mouthwash according to claim 1, including from 0.10 to about 0.5 percent by weight of lemon oil, wherein said weight ratio of surfactant to lemon oil is greater than 5 to 1.

9. A mouthwash according to claim 8, wherein the weight ratio of said surfactant to said lemon oil is about 10 to 1.

10. A mouthwash according to claim 9, wherein said pH is from about 5 to about 6.

11. A mouthwash according to claim 9, wherein said buffering agent is chosen from the group consisting of alkali metal salts of weak organic acids and is present in an amount of about 0.1 to 1.0 percent by weight.

12. A mouthwash according to claim 11, wherein said buffering agent is sodium benzoate.

13. A mouthwash according to claim 4, wherein said antibacterial agent is benzethonium chloride.

14. A mouthwash formulation according to claim 1 having a viscosity at room temperature from about 1.0 cps to about 10.0 cps.

15. A mouthwash according to claim 3 further containing about 1 to 2 percent by weight of a flavoring denaturing agent for said alcohol selected from the group consisting of anethol, anise oil, bay oil (cyrcia oil), benzaldehyde, bergamot oil, bitter almond oil, camphor, cedar leaf oil, chorothymol, cinnamic aldehyde, cinnamon oil, citronella oil, clove oil, coal tar, eucalyptol, eucalyptus oil, eugenol, guaiacol, lavender oil, menthol, mustard oil, peppermint oil, phenol, phenyl salicylate, pine oil, pine needle oil, rosemary oil, sassafras oil, spearmint oil, spike lavender oil, storax, thyme oil, thymol, tolu balsam, turpentine oil, wintergreen oil and boric acid.

16. A mouthwash according to claim 11 wherein said salt is selected from the group consisting of sodium benzoate, sodium citrate, potassium tartarate and sodium phosphate.

17. A mouthwash as defined in claim 4 wherein said antibacterial agent is selected from the group consisting of benzethonium chloride, N-alkylpyridinium chloride, N-cetyl pyrridinium bromide, sodium N-lauroyl sarcosine, sodium N-palmitoyl sarcosine, lauroyl sarcosine, N-myristoyl glycine and potassium N-lauroyl sarcosine.

18. A mouthwash according to claim 1 wherein said surfactant is selected from the group consisting of polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate and polyoxyethylene sorbitan trioleate.

* * * * *